US012679729B2

(12) United States Patent
Fine et al.

(10) Patent No.: US 12,679,729 B2
(45) Date of Patent: Jul. 14, 2026

(54) CONVERSION OF NITROGEN DIOXIDE (NO₂) TO NITRIC OXIDE (NO)

(71) Applicant: VERO BIOTECH INC., Atlanta, GA (US)

(72) Inventors: David H. Fine, Cocoa Beach, FL (US); Gregory Vasquez, Cocoa, FL (US); David P. Rounbehler, Lexington, MA (US)

(73) Assignee: VERO Biotech Inc., Atlanta, GA (US)

( * ) Notice: Subject to any disclaimer, the term of this patent is extended or adjusted under 35 U.S.C. 154(b) by 4 days.

(21) Appl. No.: 18/532,511

(22) Filed: Dec. 7, 2023

(65) Prior Publication Data

US 2024/0367975 A1     Nov. 7, 2024

Related U.S. Application Data

(60) Continuation of application No. 17/727,489, filed on Apr. 22, 2022, now Pat. No. 11,884,541, which is a (Continued)

(51) Int. Cl.

| | |
|---|---|
| *B01D 53/02* | (2006.01) |
| *A61D 7/04* | (2006.01) |
| *A61K 33/00* | (2006.01) |
| *A61M 16/00* | (2006.01) |
| *A61M 16/10* | (2006.01) |

(Continued)

(52) U.S. Cl.
CPC ............... *C01B 21/32* (2013.01); *A61D 7/04* (2013.01); *A61K 33/00* (2013.01); *A61M 16/0051* (2013.01); *A61M 16/0057* (2013.01); *A61M 16/009* (2013.01); *A61M 16/104* (2013.01); *A61M 16/1075* (2013.01); *A61M*

*16/12* (2013.01); *A61M 16/16* (2013.01); *C01B 21/24* (2013.01); *G01N 27/416* (2013.01); *A61M 2016/102* (2013.01); *A61M 16/1055* (2013.01);

(Continued)

(58) Field of Classification Search
CPC ..... A61D 7/04; A61K 33/00; A61M 16/0051; A61M 16/0057; A61M 16/009; A61M 16/104; A61M 16/1055; A61M 16/107; A61M 16/1075; A61M 16/12; A61M 16/16; A61M 2016/102; A61M 2202/0275; A61P 11/00; A61P 11/06; A61P 9/08; A61P 9/12; C01B 21/24; C01B 21/32; G01N 27/416; Y10T 436/179228
See application file for complete search history.

(56) References Cited

U.S. PATENT DOCUMENTS

2006/0180147 A1 *  8/2006  Rounbehler ........ A61M 16/122
                                                128/203.12

* cited by examiner

*Primary Examiner* — Christopher P Jones
(74) *Attorney, Agent, or Firm* — Meunier Carlin & Curfman LLC

(57) ABSTRACT

Various systems, devices, NO₂ absorbents, NO₂ scavengers and NO₂ recuperator for generating nitric oxide are disclosed herein. According to one embodiment, an apparatus for converting nitrogen dioxide to nitric oxide can include a receptacle including an inlet, an outlet, a surface-active material coated with an aqueous solution of ascorbic acid and an absorbent wherein the inlet is configured to receive a gas flow and fluidly communicate the gas flow to the outlet through the surface-active material and the absorbent such that nitrogen dioxide in the gas flow is converted to nitric oxide.

13 Claims, 9 Drawing Sheets

Outlet ◄──────      ──────► Inlet
                                              316

Related U.S. Application Data division of application No. 16/512,021, filed on Jul. 15, 2019, now Pat. No. 11,312,626, which is a continuation of application No. 16/140,497, filed on Sep. 24, 2018, now abandoned, which is a continuation of application No. 15/645,197, filed on Jul. 10, 2017, now Pat. No. 10,081,544, which is a continuation of application No. 14/294,070, filed on Jun. 2, 2014, now Pat. No. 9,701,538, which is a continuation of application No. 14/107,535, filed on Dec. 16, 2013, now Pat. No. 8,741,222, which is a continuation of application No. 13/480,376, filed on May 24, 2012, now Pat. No. 8,609,026, which is a division of application No. 13/072,466, filed on Mar. 25, 2011, now Pat. No. 8,187,544, which is a division of application No. 12/361,274, filed on Jan. 28, 2009, now Pat. No. 7,914,743.

(60) Provisional application No. 61/024,178, filed on Jan. 28, 2008.

(51) Int. Cl.
| | |
|---|---|
| *A61M 16/12* | (2006.01) |
| *A61M 16/16* | (2006.01) |
| *C01B 21/24* | (2006.01) |
| *C01B 21/32* | (2006.01) |
| *G01N 27/416* | (2006.01) |

(52) U.S. Cl.
CPC ... *A61M 16/107* (2014.02); *A61M 2202/0275* (2013.01); *Y10T 436/179228* (2015.01)

Outlet ◄——          Inlet

316

312          314

310

316

310

340          330

320

Air Flow
Pattern

Side View

Top View

⟹ Inlet/Outlet
◎ Charcoal Powder
☺ Silica or Ascorbic Acid

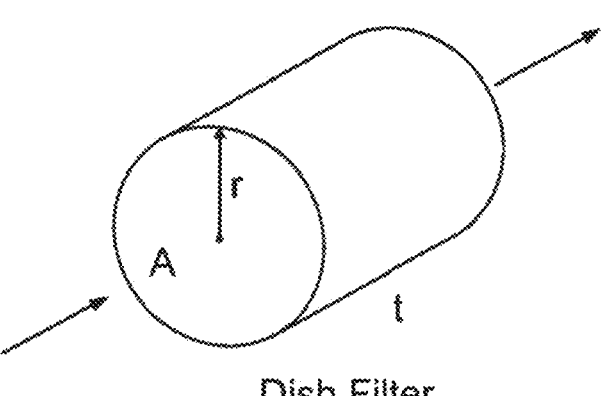
Dish Filter
Figure 9A
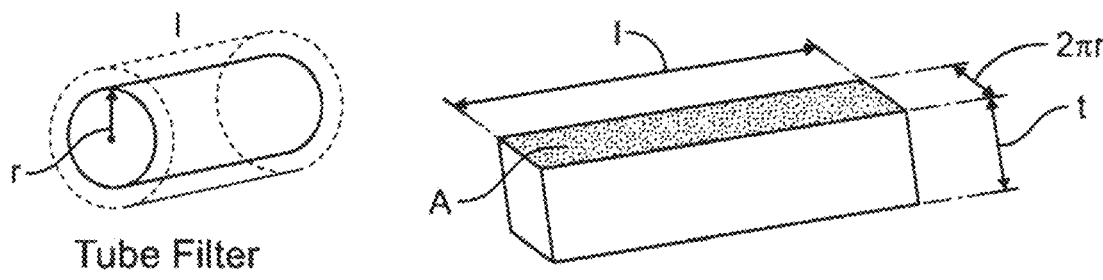
Tube Filter
Figure 9B
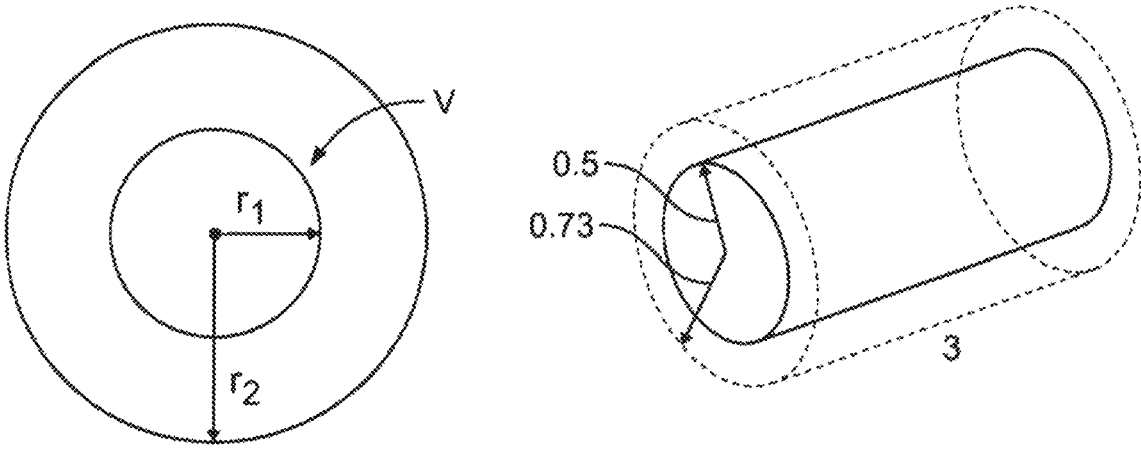
Figure 9C                    Figure 9D

CONVERSION OF NITROGEN DIOXIDE (NO₂) TO NITRIC OXIDE (NO)

CLAIM OF PRIORITY

This application is a continuation of U.S. application Ser. No. 17/727,489, filed on Apr. 22, 2022, now U.S. Pat. No. 11,884,541, which is a division of U.S. patent application Ser. No. 16/512,021, filed on Jul. 15, 2019, now U.S. Pat. No. 11,312,626, which is a continuation of U.S. patent application Ser. No. 16/140,497, filed on Sep. 24, 2018, which is a continuation of U.S. patent application Ser. No. 15/645,197, filed on Jul. 10, 2017, now U.S. Pat. No. 10,081,544, which is a continuation of U.S. patent application Ser. No. 14/294,070, filed on Jun. 2, 2014, now U.S. Pat. No. 9,701,538, which is a continuation of U.S. patent Ser. No. 14/107,535, filed on Dec. 16, 2013, now U.S. Pat. No. 8,741,222, which is a continuation of U.S. patent application Ser. No. 13/480,376, filed on May 24, 2012, now U.S. Pat. No. 8,609,026, which is a division of U.S. patent application Ser. No. 13/072,466, filed on Mar. 25, 2011, now U.S. patent Ser. No. 8/187,544, which is a division of U.S. patent application Ser. No. 12/361,274, filed on Jan. 28, 2009, now U.S. Pat. No. 7,914,743, which claims the benefit of prior U.S. Provisional Application No. 61/024,178, filed on Jan. 28, 2008, each of which are incorporated by reference in their entirety.

TECHNICAL FIELD

This description relates to controlled generation of nitric oxide.

BACKGROUND

Nitric oxide (NO), also known as nitrosyl radical, is a free radical that is an important signaling molecule in pulmonary vessels. Nitric oxide (NO) can moderate pulmonary hypertension caused by elevation of the pulmonary arterial pressure. Inhaling low concentrations of nitric oxide (NO), for example, in the range of 2-100 ppm can rapidly and safely decrease pulmonary hypertension in a mammal by vasodilation of pulmonary vessels.

Some disorders or physiological conditions can be mediated by inhalation of nitric oxide (NO). The use of low concentrations of inhaled nitric oxide (NO) can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide (NO) can also be used to treat chronic pulmonary hypertension, bronchopulmonary dysplasia, chronic pulmonary thromboembolism and idiopathic or primary pulmonary hypertension or chronic hypoxia. Typically, the NO gas is supplied in a bottled gaseous form diluted in nitrogen gas (N₂). Great care has to be taken to prevent the presence of even trace amounts of oxygen (O₂) in the tank of NO gas because the NO, in the presence of O₂, is oxidized to nitrogen dioxide (NO₂). Unlike NO, the part per million levels of NO₂ gas is highly toxic if inhaled and can form nitric and nitrous acid in the lungs.

SUMMARY

In one aspect. an apparatus for converting nitrogen dioxide to nitric oxide includes a receptacle including an inlet, an outlet, a surface-active material coated with an aqueous solution of ascorbic acid and an absorbent, wherein the inlet is configured to receive a gas flow and fluidly communicate the gas flow to the outlet through the surface-active material and the absorbent such that nitrogen dioxide in the gas flow is converted to nitric oxide. The absorbent can be silica gel or activated alumina.

In another aspect, a method of providing a therapeutic amount of nitric oxide to a mammal includes diffusing nitrogen dioxide into a gas flow, exposing the nitrogen dioxide to a surface-active material coated with ascorbic acid and an absorbent to eliminate the by-products of ascorbic acid oxidation and transporting the nitric oxide in a therapeutic amount to a mammal.

In a further aspect, a system of delivering a therapeutic amount of nitric oxide to a mammal includes a gas source of nitric oxide; and a NO₂ scavenger selected from the group consisting of proline and diphenylamine.

In one aspect, a recuperator for converting nitrogen dioxide into nitric oxide includes an exit shell including an outlet, an inside shell wherein the inside shell includes perforated inner and outer tubes with fixed annulus, a surface-active material coated with an aqueous solution of ascorbic acid, an absorbent and a top cap including an inlet wherein the inlet is configured to receive a gas flow and fluidly communicate the gas flow to the outlet through the surface-active material such that nitrogen dioxide in the gas flow is converted to nitric oxide. The recuperator further includes an annular ring around the top cap.

In another aspect, a system for delivering nitric oxide to a patient, includes a gas source of nitrogen dioxide, dinitrogen tetraoxide, or nitric oxide, a first device having an inlet, an outlet, and a porous solid matrix positioned between the inlet and the outlet, wherein the porous solid matrix is coated with an aqueous solution of an antioxidant, and wherein the inlet is configured to receive a gas flow from the source and fluidly communicate the gas flow to the outlet through the porous solid matrix to convert nitrogen dioxide in the gas flow into nitric oxide, and a recuperator coupled to the outlet of the first device, the recuperator converting nitrogen dioxide into nitric oxide prior to delivery to the patient. The recuperator can have a flow resistance of less than 3 cm of water pressure at a flow of 60 L/minute. The recuperator can have a flow resistance of less than 1 cm water at 15 L/min. The recuperator can operate at atmospheric pressure. The recuperator can have an oxygen concentration of in the range of 21 to 100%. The recuperator can have a humidity of dry to 99% (non condensing). The recuperator can be thermally insulated. The recuperator can be coupled to the outlet of a first device through a humidified line. The humidified line can be heated. The humidified line can be heated to about 35° C. The recuperator can be coupled to a NO/NO₂ gas analyzer. The recuperator can further include a particle filter.

In a further aspect, a method of sampling NO and NO₂ gas in a NO delivery system includes obtaining a sample of gas, diluting the sample of gas with air, and measuring the amount of NO and NO₂ gas with a gas analyzer. The sample of gas can be diluted by 50%. The sample of gas can be diluted by 33%. The sample of gas can be diluted with air from the hospital room. The sample of gas can be diluted with air from the wall. The sample of gas can be diluted with oxygen.

The details of one or more embodiments of the invention are set forth in the accompanying drawings and the description below. Other features, objects, and advantages of the invention will be apparent from the description and drawings, and from the claims.

DESCRIPTION OF DRAWING

FIGS. 9A-D are diagrams depicting geometrical depictions of dish filters and tube filters.

DETAILED DESCRIPTION

Figure 1:
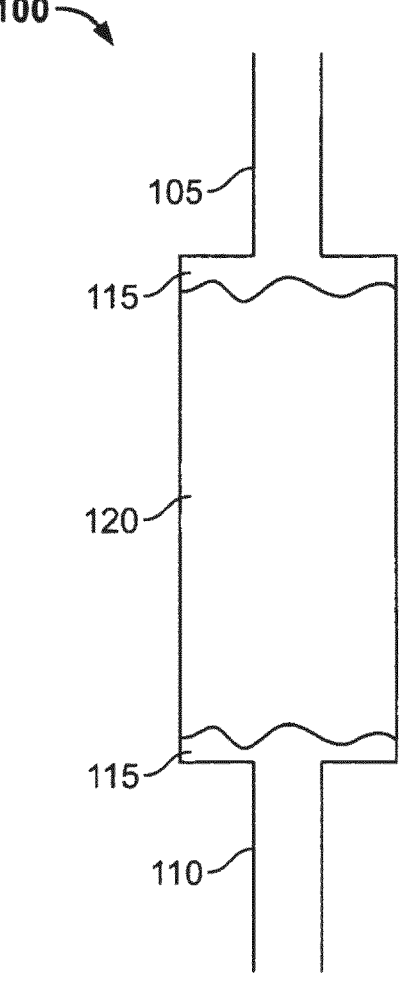
FIG. 1 is a block diagram of a cartridge that converts $NO_2$ to NO.

Nitric Oxide (NO) is very well known and well-studied gas. NO is normally present in the atmosphere (as a pollutant from automobiles and power plants) at concentrations between 0.010 and 0.500 parts per million (ppm), and NO concentrations may reach 1.5 ppm in heavy traffic. NO is also present in tobacco smoke at levels as high as 500 ppm to 2000 ppm.

For medical applications, NO gas, like oxygen has been studied and used to treat patients for many years. In biological systems, NO is a molecule that is naturally produced in the human body. NO is one of the few gaseous signaling molecules known. NO is a key vertebrate biological messenger, playing a role in a variety of biological processes. NO is highly reactive (having a lifetime of a few seconds), yet diffuses freely across membranes. These attributes make NO ideal for a transient signal molecule between adjacent cells and within cells. Several pharmaceutical products, such as Nitroglycerin, amyl nitrite and Sildenafil (Viagra) serve as vasodilators because they either release or cause NO to be released in the body. In 1987, the biologic similarities of NO to endothelium-derived relaxing factor were demonstrated. Subsequently, NO and endothelium-derived relaxing factor were considered the same entity. During the late 1980s and early 1990s, inhaled NO emerged as a potential therapy for the acute respiratory distress syndrome (ARDS), sickle cell anemia, COPD and other conditions. Since then NO has been shown to reduce persistent pulmonary hypertension and also to reduce pulmonary hypertension without any undesired drop in systemic blood pressure, which is valuable when treating heart and lung transplant patients and other patients having undergone interventional cardiovascular procedures. The gas was readily available for many years from several suppliers as were several competing CE marked delivery systems. During the 1990s the medical use of the gas was patented and the cost has increased substantially. Even with this restriction, NO is currently routinely and safely used under institutional or countywide protocols for many uses outside of the approved indications for neonates.

When delivering NO for therapeutic use to a mammal, it can be important to avoid delivery of nitrogen dioxide $NO_2$ to the mammal. $NO_2$ can be formed by the oxidation of NO with oxygen ($O_2$). The rate of formation of $NO_2$ is proportional to the $O_2$ concentration multiplied by the square of the NO concentration—that is, $(O_2)*(NO)*(NO)=NO_2$.

In one aspect, a NO delivery system that converts $NO_2$ to NO is provided. The system employs a surface-active material coated with an aqueous solution of antioxidant as a simple and effective mechanism for making the conversion. One example of a surface-active material is silica gel. Another example of a surface-active material that could be used is cotton. The surface-active material may be or may include a substrate capable of retaining water. Another type of surface-active material that has a large surface area that is capable of absorbing moisture also may be used. More particularly, $NO_2$ can be converted to NO by passing the dilute gaseous $NO_2$ over a surface-active material coated with an aqueous solution of antioxidant. When the aqueous antioxidant is ascorbic acid (that is, vitamin C), the reaction is quantitative at ambient temperatures.

The oxidation of ascorbic acid with oxygen under moist conditions can be complex, with over 50 different compounds having been reported. (See J. C. Deutsch, "Spontaneous hydrolysis and dehydration of dehydroa," *Analytical Biochemistry*, Vol. 260, no. 2, pages 223-229 (Jul. 1, 1998); Dong Bum Shin and Milton S. Feather, "3-deoxy-L-glycero-pentos-2-ulose (3-deoxy-L-xylosone) and L-threo-pentos-2-ulose (L-xylosone) as intermediates in the degradation of L-ascorbic acid," *Carbohydrate Research*. Vol. 280, pages 246-250 (Dec. 15, 1990); Eiji Kimoto et al., "Analysis of the transformation products of dehydro-L-ascorbic acid by ion-pairing high-performance liquid chromatography," *Analytical Biochemistry*, Vol. 214, pages 38-44 (1993), Academic Press; Steven R. Tannenbaum et al., "Inhibition of nitrosamine formation by ascorbic acid," *The American Journal of Clinical Nutrition*, Vol. 53 (1 Suppl.) pages 247S-250S (January 1990), all of which are incorporated by reference in their entireties). The reaction generally leads to dehydroxy ascorbic acid, which can then be further degraded into multiple species.

FIG. 1 illustrates an example of a cartridge 100 for generating NO by converting $NO_2$ to NO. The cartridge 100, which may be referred to as a NO generation cartridge, a cartridge, or a cylinder, includes an inlet 105 and an outlet 110. Screen and glass wool 115 are located at both the inlet 105 and the outlet 110, and the remainder of the cartridge 100 is filled with a surface-active material 120 that is soaked with a saturated solution of antioxidant in water to coat the surface-active material. The surface-active material can be silica gel. The screen and glass wool 115 also is soaked with the saturated solution of antioxidant in water before being inserted into the cartridge 100. In the example of FIG. 1, the antioxidant can include ascorbic acid. In other embodiments, the antioxidant can include alpha tocopherol or gamma tocopherol.

The moist silica gel of the cartridge can adsorb and bind up the vast majority of the products of the side reactions.

In the presence of moisture, oxygen and NO, $NO_2$ forms $N_2O_3$, $N_2O_4$ and the nitrite ion. In one embodiment, these reactants can combine with an $NO_2$ scavenger which can include the common amino acid, proline, to form N-nitroso proline. N-nitrosproline is non carcinogenic. This reaction has been used in vivo by Tannenbaum *The American Journal of Clinical Nutrition*, Vol. 53 (1 Suppl.) pages 247S-250S (January 1990), and Ohshima and Bartsch (*Cancer Res.* Vol. 41, p. 3658-3662 (1981), to measure the nitrosation capacity of the body, and to show that the addition of Vitamin C can reduce this capacity. Such a reaction can be used to trap out $NO_2$ in the gas phase from an air stream containing moist $NO_2$ in the presence of oxygen and NO. The proline can be in the form of a crystalline powder. Proline can be placed in a tube and gas can be allowed to flow over it. The $NO_2$ that is present can bind irreversibly with the proline to form N-nitroso proline. The application of this reaction is to use this reaction as a scavenger to remove the last minute traces of $NO_2$ from an air stream containing NO and oxygen and air. In one embodiment, such a $NO_2$ scavenger can be used in a NO delivery system to allow any $NO_2$ that is present to bind irreversibly with the proline to form N-nitroso proline.

The proline can be in the form of a powder, or as a solution that has been deposited onto a substrate such as silica gel, activated alumina and charcoal. Other appropriate substrates can be used as long as proline is available to react with $NO_2$ gas. In one embodiment, an aqueous solution of proline in water can be used. In another embodiment, diphenylamine or any secondary or tertiary amine can be used to react with $NO_2$ gas. Examples of secondary amines can include dimethylamine, methylethanolamine or 2-(methylamino)ethanol, cyclic amines such as aziridine, azetidine, pyrrolidine and piperidine. Examples of tertiary amine can include trimethylamine, dimethylethanolamine (DMEA), 2-(dimethylamino)ethanol or bis-tris.

Preferably, any material can be used where the Nitroso product will not be carcinogenic or toxic. In other embodiments, any compounds that bind with the $NO_2$ to form organic compounds can be used. Products include but are not limited to: nitro, nitroso, or azo as long as the $NO_2$ is chemically bound up so as to remove it from the system.

In one embodiment, an $NO_2$ scavenger can be included in a NO delivery system. The purpose of the $NO_2$ scavenger is to remove any $NO_2$ gas that may have been formed in the ventilator and during storage in a gas bag or other temporary gas storage device. In another embodiment, the $NO_2$ scavenger can remove $NO_2$ that is formed in the gas plumbing lines from the exit of the NO generation cartridge. The $NO_2$ scavenger can serve as a safety device to reduce the $NO_2$ levels to below 0.1 ppm, at any flow and at any NO concentration, prior to delivery to a patient.

In another aspect, a recuperator is included in the NO delivery system. The purpose of the recuperator is to convert any $NO_2$ gas that may have been formed in the ventilator and during storage in a gas bag or other temporary gas storage device to NO. In one embodiment, the recuperator is a device that is immediately adjacent to the patient. It serves the same purpose as the main NO generation cartridge, namely to convert $NO_2$ to NO. In another embodiment, the recuperator coverts $NO_2$ that is formed in the gas plumbing lines from the exit of the cylinder NO generation cartridge to NO. The recuperator can be a cartridge that is needed to recover any $NO_2$ that was formed in the ventilator and in the gas lines from the reaction of NO and Oxygen. The recuperator can serve as a safety device to reduce the $NO_2$ levels to below 0.1 ppm, at any flow and at any NO concentration, prior to delivery to a patient.

In one embodiment, the flow resistance for the recuperator can be as low as possible, for example, less than 3 cm of water pressure at a flow of 60 L/minute, and/or <1 cm water at 15 L/min. The recuperator can operate at atmospheric pressure. The oxygen concentration at the recuperator can be in the range of 21% to 100%. The humidity at the recuperator can be 0% to 99%. The recuperator can be thermally insulated to prevent water condensation. The inlet to the recuperator can be from the humidified (and heated) line that is delivering gas to the patient. This line can be typically heated to about 35° C. to prevent water condensation in the lines.

The exit side of the recuperator can be a sample probe that goes to the NO/$NO_2$ gas analyzer. The sample line can be diluted with an equal volume of air so as to reduce the relative humidity and to minimize the rate of formation of $NO_2$ from Oxygen in the sample line to the analyzer. The weight of the recuperator can be kept as low as possible, so that it is not unwieldy, under 2 pounds but preferably under 1 pound or under 0.5 pounds. The exit from the recuperator can go directly to the patient by means of a short (approximately 6 inch) length of roughly 1 inch diameter ventilator tubing. The recuperator can be disposable and can be for a single use only. The recuperator can incorporate a particle filter to prevent any possibility that trace amounts of dust from the recuperator being delivered to a patient, for example, fine silica gel or ascorbic acid for the recuperator, or fine proline for the scavenger. The same filter material will also prevent bacteria and other particles from being delivered to the patient.

Figure 2A:
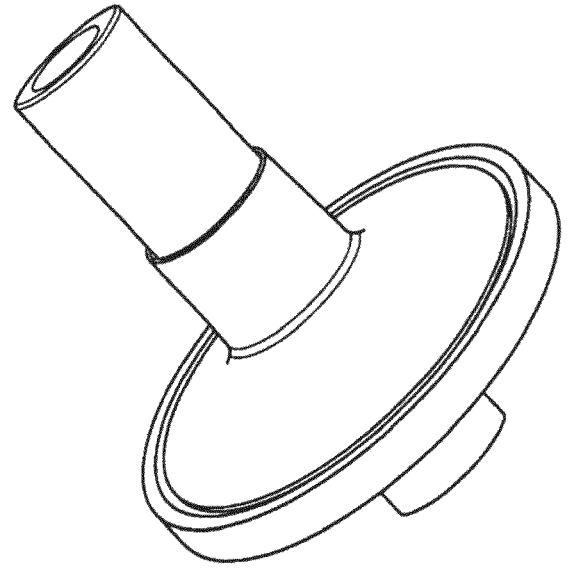
FIGS. 2A-B are diagrams depicting implementations of a disc filter recuperator.
Figures 3A, 3B:
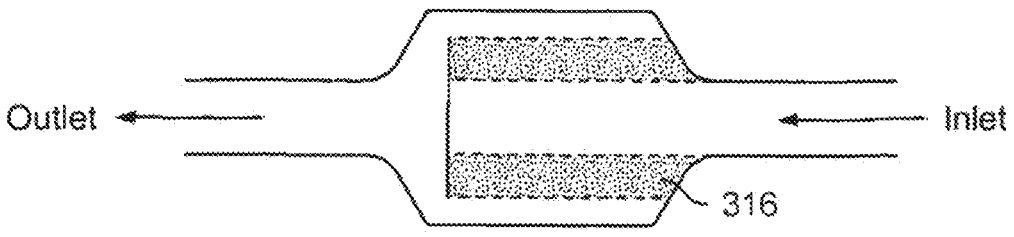
FIGS. 3A-B are diagrams depicting implementations of a tubular filter recuperator.

In one embodiment, the recuperator is provided as a disc as exemplified in FIGS. 2A and B. In a further embodiment, the recuperator can include a common filter design that is widely used in industry which is a tubular design with co-axial tubes. This type of design is especially common in water filters and for use in compressed in air lines. In another embodiment, the recuperator is provided as a tubular filter as exemplified in FIGS. 3A and B. As depicted in FIGS. 3A and B, the tubular filter can be constructed from three concentric tubes, with the filter medium being held tightly in place in a perforated section of the interior. The tubular filter can hold the silica gel or ascorbic acid dust in place in the annulus between the two perforated tubes. A filter medium can be placed on both contact sides of the silica gel or ascorbic acid dust. The powder or dust can be compressed during filing without the compression material coming into contact with the flowing air stream. The aspect ratio will be easier to handle adjacent to the patient, where a small diameter shape can be used. The tubular filter can include an exit shell as depicted in FIG. 3B, an inside shell that includes perforated inner and outer tubes with fixed annulus and an annulus filled with silica gel or ascorbic acid dust. The inner and outer annulus can be lined with filter material. In one embodiment, the final assembly of the tubular filter is depicted in FIG. 3B. The final assembly can include a top cap and an annular ring at the top can keep pressure on the silica gel or ascorbic acid dust.

In one embodiment, a method of NO and $NO_2$ gas sampling is provided. For example, for 100 ppm of NO and 100% oxygen, 1.70 ppm of $NO_2$ can be formed in the gas sampling lines from the reaction of NO with oxygen. The problem is how to sample for $NO_2$ in a gas stream that has the reaction of NO and oxygen going on at the same time. This is made worse at high NO concentrations. For example at 200 ppm NO the rate of formation of $NO_2$ in the sample line is 4 times the rate as compared to 100 ppm. Also at 100% oxygen the rate is 5 times the rate in air. To get an accurate reading of what was in the line at the patient there is a need to either sample quickly, or slow the reaction down somehow. By diluting by 50%, the rate is decreased 4 fold due to the drop in NO concentration and approximately 2.5 fold by the drop in Oxygen concentration.

In one embodiment, the sample tube from the patient to the detector can be diluted up to 66%, or up to 50% or up to 33%. The sample can be diluted at the sample point. The sample can be diluted with air. For example, dilution of one part sample and one part with air can reduce the water concentration in the sample. In another embodiment, the sample can also be diluted as follows: one part sample and two parts with air from the room (e.g. hospital room). Alternatively, the sample can also be diluted using bone dry air from the wall.

In a further embodiment, the sample tube can be spliced in two or three, adjacent to the sampling point on the recuperator. This can be done for 50 or 66% dilution.

Examples

Gas Cylinder Cartridge Design

In another aspect, the gas cylinder and appropriate amount of $NO_2$ for clinical use is provided. The FDA standard room size: $3.1 \times 6.2 \times 4.65$ m=89.3 m$^3$=89,300 L. The OSHA $NO_2$ level is 5 ppm. All the three gas cylinders described herein are approximately equivalent in the amount of gas that they can deliver.

Size AS of the cylinder is pressurized to 2000 psi. The sudden release of the entire contents of 3600 L of 124 ppm would lead to a $NO_2$ level of 5.0 ppm in the room, if there was no air exchange. Thus, in order to meet the current FDA requirement for safety, the highest concentration in a gas cylinder of this size and type should be 100 ppm of $NO_2$ (with a built in safety factor). The cylinder that is used in the lab will deliver 3,600 liters of gas (without dilution) containing 100 ppm of $NO_2$. At 5 L/min, this gas cylinder will last for 720 minutes=12 hours. At 48 pounds, without the regulator and top, this cylinder is far too heavy to be picked up by a nurse or therapist, and has to be moved on a wheeled cart.

Size AQ/BL/88 2000 psi cylinder is currently in use in hospitals. The sudden release of the entire contents of 1918 L of 233 ppm would lead to a $NO_2$ level in the hypothetical room of 5.0 ppm. Thus, in order to meet the current FDA requirement for safety, the highest concentration in a gas cylinder of this size and type should be 200 ppm of $NO_2$ (with a built in safety factor). For a cylinder of this size and 200 ppm of $NO_2$, the ideal oxygen level would be 70-74%. This pressure cylinder will deliver 3836 liters of gas (after dilution) containing 100 ppm of $NO_2$. At 5 L/min, this gas cylinder will last 767 minutes=12.8 hours. This cylinder weighs 30 pounds and is still too heavy to be picked up by a nurse. It is a bit more maneuverable but still needs a wheeled cart for transport.

Luxfer's ME36 3000 psi cylinder holds 992 Liters at a pressure of 3000 psi instead of 2000 psi. The sudden release of the entire contents of 992 L of 450 ppm would lead to a $NO_2$ level of 5.0 ppm in the hypothetical room. Thus, in order to meet the current FDA requirement for safety, the highest concentration in a gas cylinder of this size and type should be 400 ppm of $NO_2$ (with a built in safety factor). This cylinder however, weighs only 8.3 pounds compared to INO's 30 pounds. The contents of this small, high pressure cylinder would last as long as the AQ and the AS. This translates into the cylinders being used up at twice or four times the rate of INO but at less than $\frac{1}{3}^{rd}$ of the weight this is a reasonable trade off. The key advantage is that the cylinder is small and light enough to be stocked in a pharmacy and picked up by a nurse with one hand. The ideal oxygen level in a cylinder of this size would be about 60%. The Luxfer high pressure miniature gas cylinder will deliver 3968 liters of gas (with dilution) containing 100 ppm of $NO_2$. At 5 L/min, this gas cylinder will last 793 minutes=13.2 hours. At only 8.3 pounds, this cylinder can be picked up by a nurse with one hand. It is small enough to be stored in a hospital pharmacy. The 3000 PSI Luxfer Cylinder offers the best performance and is the preferred package. Table 1 shows the specifications of the cylinders described herein.

Figure 4:
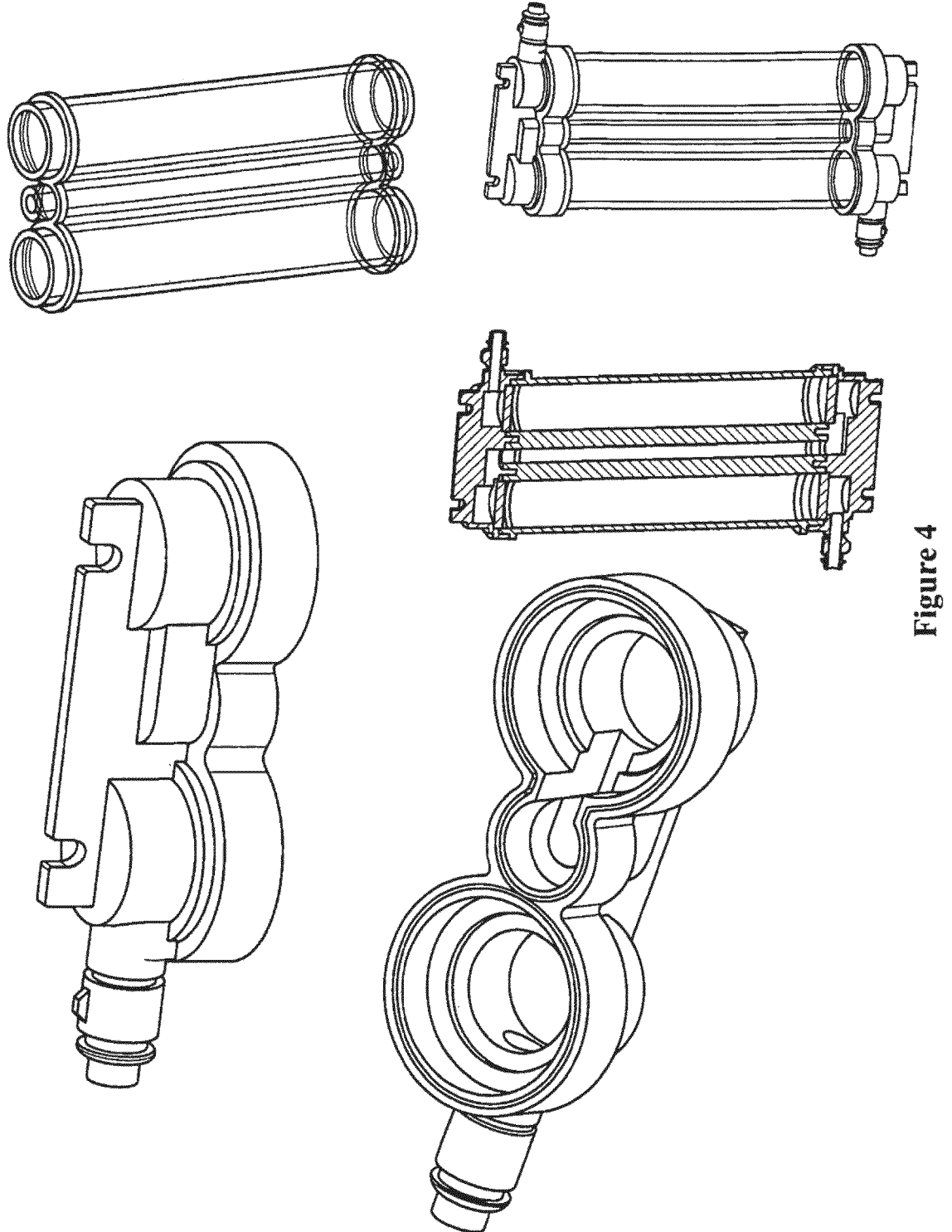
FIG. 4 is a diagram depicting an implementation of a recuperator.

The physical layout of the recuperator is able to accommodate the 4.5 inch diameter cylinder, and an output tube that contains activated charcoal powder. As an example, a tube design is exemplified in FIG. 4.

Figure 5:
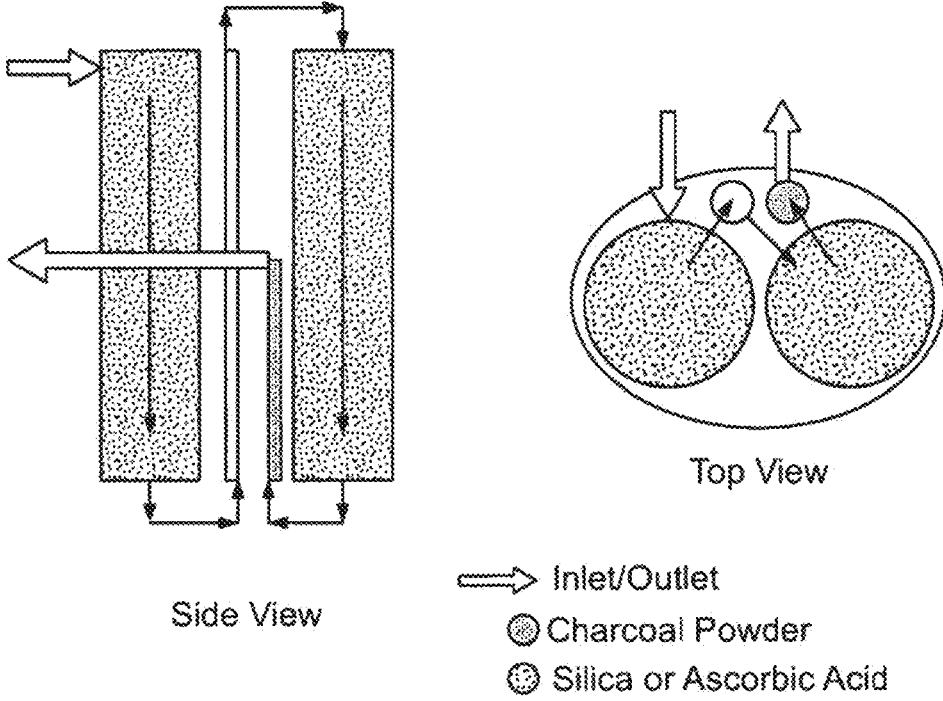
FIG. 5 is a diagram depicting another implementation of a recuperator.
Figure 6A:
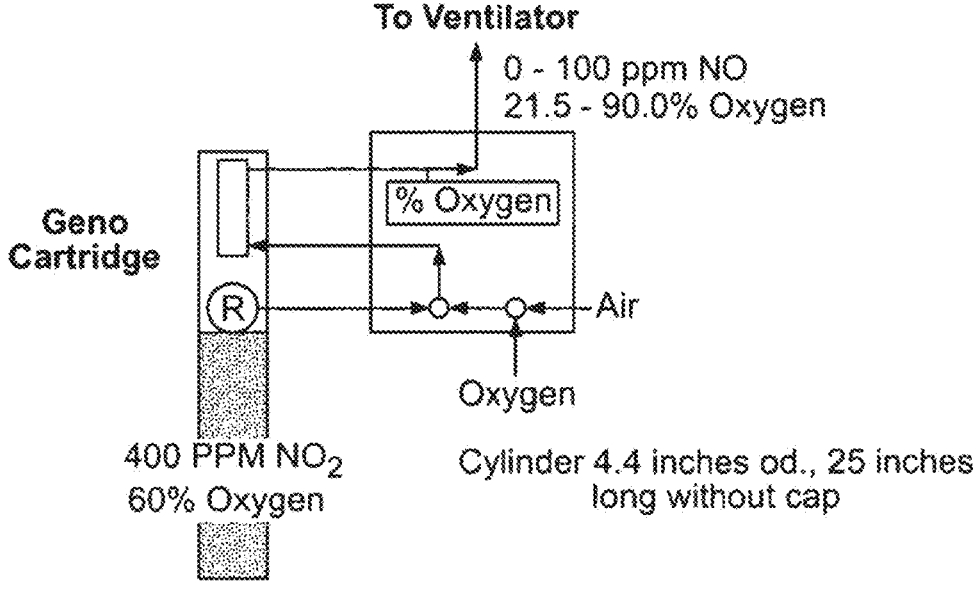
FIGS. 6A and B are flow diagrams depicting Nitric Oxide (NO) delivery systems and flow of the gasses.
Figure 6B:
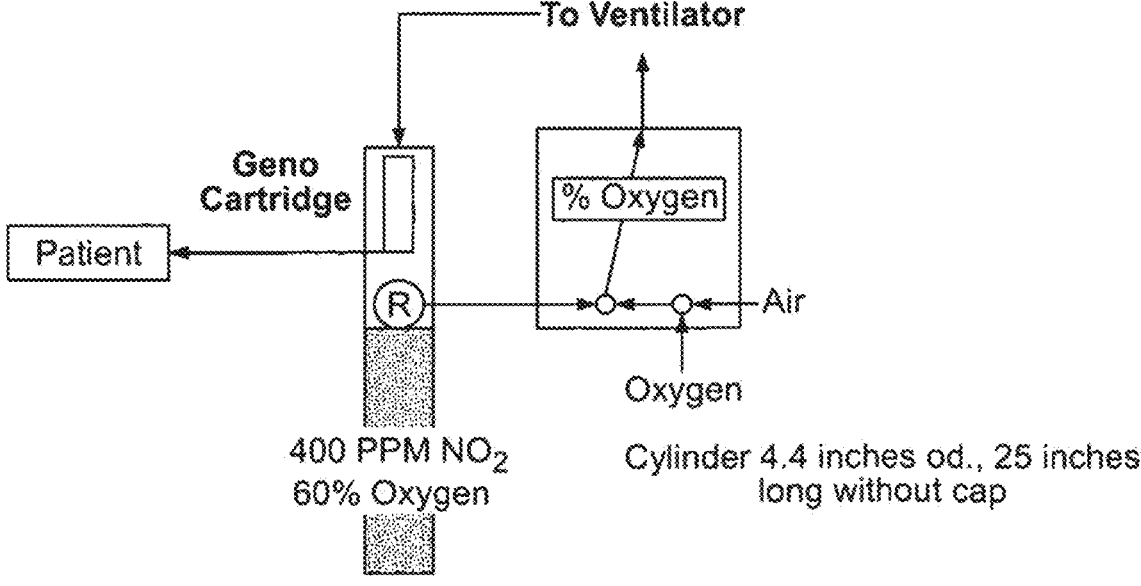

The revised design depicted in FIG. 5 has the two main tubes as close together as possible, with the small vertical tubes tucked in close. The entire package has to fit inside a 4.5 inch or less gas cylinder top. This is shown schematically in FIG. 5. Each main tube that holds the ascorbic acid/silica gel dust has an inside diameter of about 1 inch. The inlet and outlet tubes need to be on the same side. The short tube can contain a small amount of activated charcoal to remove traces of acetaldehyde. Several embodiments of the entire package for use in an Intensive Care Unit are depicted in FIGS. 6A and B.

The gas bottle contains a mixture of 60% oxygen with the balance being $N_2$. The gas also contains about 400 ppm of $NO_2$. This gas leaves the gas cylinder through a built in regulator where the pressure is reduced to the 20 to 100 psi level. The gas is attached to a separate blending box by means of a unique quick disconnect.

The gas containing 400 ppm $NO_2$ is then blended with an air/oxygen mixture to reduce the $NO_2$ concentration to the therapeutic concentration. In current use, this is 0.1 to 80 ppm. In one aspect of the system, this could be extended upwards to >200 ppm. The blender dial is calibrated in ppm equivalents of NO. The gas leaving the blender flows onto the NO generation cartridge by means of a quick disconnect attachment. The air oxygen blender is a conventional design and is available commercially. The air and oxygen are typically supplied from the hospital wall supply as a utility. Alternatively, the gas can flow through the ventilator first before the cartridge to reduce the gas pressure from 50 to 20 psa.

The cartridge converts the $NO_2$ to NO. As the gas leaves the cartridge, the gas now has NO at the proper therapeutic concentration in an air oxygen blend of the appropriate oxygen concentration. The gas leaving the cartridge is connected back to the blending box by means of a quick disconnect fitting, where the oxygen concentration can be sampled and displayed. In one embodiment, an oxygen sensor can be used to precisely set the appropriate oxygen concentration.

The reason for the three connections to the blender box is to allow quick replacement of the gas cylinder. A second cylinder will be plumbed to an identical set of three quick disconnect fittings on the blender box. When a cylinder needs to be changed, a single three stack valve is used to switch from one gas cylinder to another, allowing for the empty cylinder to be replaced. This is not shown on the FIG. 6A.

The gas mixture from the blender box becomes replaces the oxygen feed on a conventional medical ventilator. The ventilator is then used in its conventional mode and can perform whatever ventilatory cycles that the therapist desires for a particular patient. The device is intended to provide the physician a mechanism for delivering a low concentration (dose) of pure NO gas in a mixture of oxygen and air. The gas passes through a mechanical or manual ventilator and travels through respiratory tubing and a mask or tube to the patient's lungs. The gas flow can be regulated by a mechanical ventilator or manual ventilation or by delivery directly to the patient from the pressurized gas tank (for spontaneously breathing patients). The device allows the physician to independently adjust the NO concentration and the oxygen concentration of the delivered gas.

Indication for Use

The device is indicated to provide pure NO gas at different concentrations in an oxygen/air mixture.

General Product Description

In one embodiment, The Nitric Oxide (NO) Generator and Delivery System include five components that work together to create, deliver and monitor pure Nitric Oxide (NO) gas in an oxygen/air mixture. The gas travels through standard anesthesia and respiratory breathing devices for inhalation by the patient. The anesthesia part is only needed to provide variable flow rates and/or to assist patients who are not breathing on their own. In its simplest form the gas bottle stands alone and the gas is converted to NO as it leaves the gas bottle. With this approach the gas is then fed into a mask or a cannula. The gas flow is provided by mechanical or manual ventilation or by the pressurization of the tank (for spontaneously breathing patients). The concentration of NO and Oxygen are determined and adjusted by the physician based on each patient's condition and needs.

Product Components

Gas Tanks

The first component is a pressurized aluminum gas tank with a small quantity of Nitrogen Dioxide ($NO_2$) gas in an Oxygen/Air mixture. This mixture cannot be inhaled without processing by the other components as it would be toxic. The tanks will come with a standard regulator to limit the pressure of the gas to the mixer. Tanks will have concentrated level of $NO_2$ gas and in a fixed Oxygen/Air ratio. These concentrations will be adjusted using the mixing system below. Tanks used or transport will be at set concentrations of $NO_2$ gas and Oxygen/Air and will not require mixing.

Mixing System

The mixing system includes two standard gas blenders that are connected and an oxygen sensor. The first mixing chamber takes medical oxygen and air, which can be provided from pressurized tanks or the hospital's gas system. A knob allows selection of the desired $FiO_2$ (fraction of inspired oxygen) of the gas to be delivered to the patient which adjusts the oxygen/air mixture in the mixing chamber as measured by the oxygen sensor. The output of this mixture is fed into a second mixing chamber where it is mixed with the $NO_2$ gas from the gas tank described above. The knob to this mixing chamber allows the physician to select the concentration of NO gas to be delivered to the patient. The output of this mixing chamber is the passed though the gas converter and purification cartridge described below. This allows variable NO and oxygen concentration levels which are independent of each other.

Gas Converter and Purification Cartridge

The gas mixture from the last mixer will flow through the Gas Converter and Purification cartridge. This cartridge will convert all $NO_2$ gas into NO gas and remove any impurities in the entire gas mixture. The concentration of NO gas will be the same as the concentration of the $NO_2$ gas as the conversion is essentially 100%. The concentration of the oxygen (oxygen/air ratio) will not be changed. The output of the cartridge will be delivered to the mechanical or manual ventilation system and appropriate pressures. Tanks used for transport will also be fitted with a flow meter to regulate the flow of the gas to the patient.

Recuperator Cartridge

The Recuperator cartridge will be placed at the patient end of the inspiratory limb of the patient's breathing tubing. This cartridge will contain the same technology as the Gas Converter The purpose of this cartridge is twofold. First, it will reconvert any $NO_2$ gas back into NO that may have formed through the reaction of the NO gas with oxygen. Second it provides bacterial and viral filtration of the delivered gas.

Disc Recuperator

The obvious format for the recuperator is to make it much like the gas cylinder device, but with the diameter of the order of 3 to 4 inches, and the cartridge depth reduced from 5.5 inches to less than 0.3 inches. A cartridge like this has a pancake shape and would look similar to the particle filters that are used with some respiratory equipment.

The equations below show how the pressure drop across the cartridge will vary as a function of radius and the depth. For a constant volume cartridge, the pressure drop varies with the fourth power of the radius.

$$V_1 = \pi r_1^2 l_1$$

$$l_1 = V_1/\pi r_1^2$$

$$p \propto l_1/\pi r_1^2 \propto \frac{V_1}{\pi r_1^2 \times \pi r_1^2} \propto \frac{V}{\pi^2 r_1^4}$$

$$\frac{p_2}{p_1} = \frac{\pi \times \pi V_2}{V_1 \times \pi \times \pi} \frac{r_1^2 \times r_1^2}{r_2^2 \times r_3^2}$$

For constant volume of material $$p_2/p_1 = \left(\frac{r_1}{r_2}\right)^4$$

If volume material is half, then $$p_2/p_1 = 0.5\left(\frac{r_1}{r_2}\right)^4$$

The gas bottle cartridge, which has a radius of 0.4 inches and a depth of 5.5 inches, has a pressure drop that was measured experimentally of 2.7 psi=187 cm $H_2O$ water. The calculations of pressure drop for various diameters are shown in Table 2. A pressure drop of 0.2-0.3 cm water at 5 L/min is needed to attain the design goal of 3.0 cm $H_2O$ at 60 L/min. In order to achieve this low a pressure drop, the diameter of the flat disc would need to be 4.0 to 4.5 inches. If it were to have the same amount of material as the current cylinder cartridge, the depth would need to be 0.56 cm at 4.00 inches and 0.44 inches at 4.5 inches.

Figure 2B:
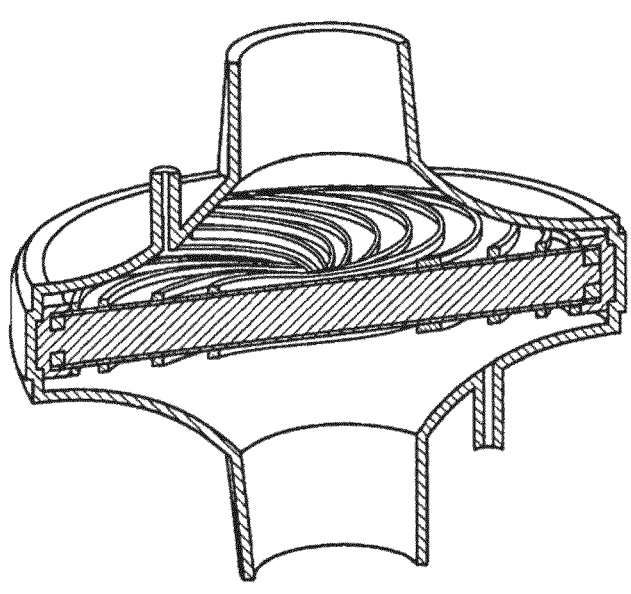
Figure 7:
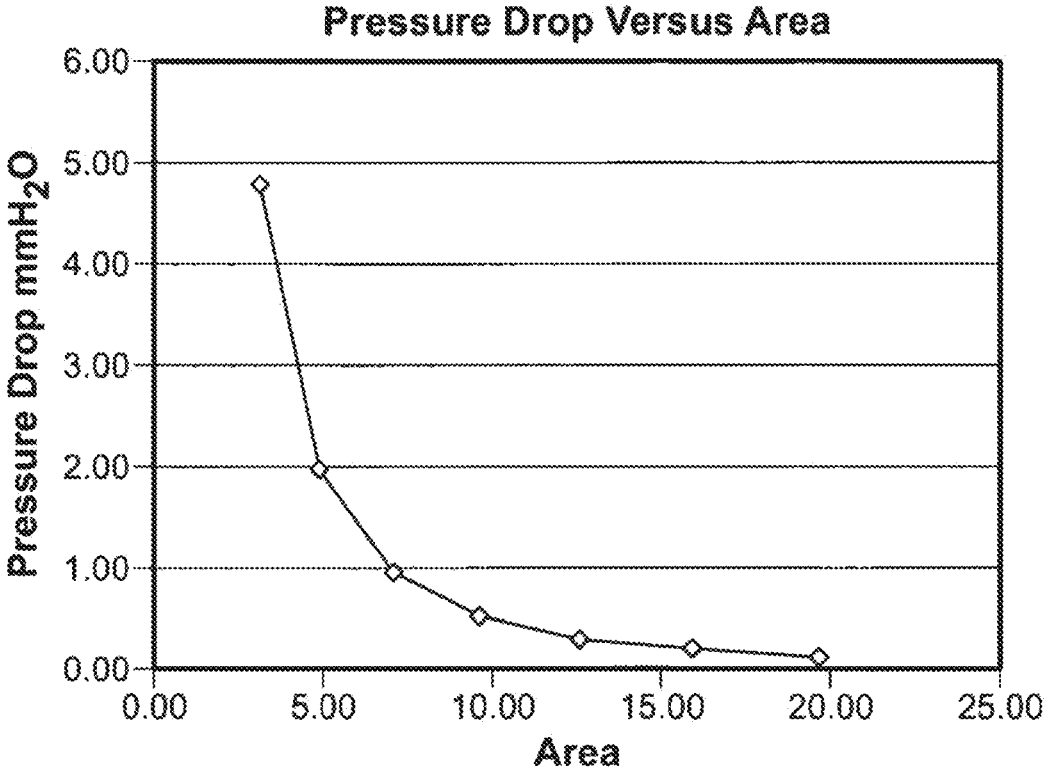
FIG. 7 is a graph depicting the variation of pressure drop with size of a disc recuperator.

A flat disc of 3 inches diameter and a 1.0 cm thickness, has been tested in the laboratory and has been shown to perform as well as the cylinder cartridge. The variation of pressure drop with size, where all the filters have the same volume of material, is shown in FIG. 7. Various concepts have been evaluated on how to build such a device. The difficulty is how to encapsulate the silica gel or ascorbic acid dust between two very thin filter cloths, and have not only uniform thickness everywhere, but also no settling of the silica gel or ascorbic acid dust. Settling would be catastrophic and could lead to channeling and failure. An example of one such design is shown in FIG. 2B.

A comparison of the pressure drop across the disc and tubular filters are shown mathematically below and in FIGS. 9A and B.

| | Dish Filter | | Tube Filter |
|---|---|---|---|
| | $A = \pi r^2$ | | $A = 2\pi r \cdot 1$ |
| | $V = \pi r^2 t$ | | $V = 2\pi r \cdot 1 \cdot t$ |
| | | | $t = \dfrac{V}{2\pi r l}$ |

For Cylinder:

$$p \propto \frac{t}{A} = \frac{t}{2\pi r l} = \frac{V}{(2\pi r l)^2} = \frac{V}{4\pi^2 r^2 l^2}$$

For Dish:

$$p \propto \frac{V}{\pi^2 r^2 r^2}$$

Essentially, the analysis shows that the pressure drop of the tubular filter, like the disc filter, is proportional to the surface area (the inner circumference of the tubular filter) and the thickness of the bed. The detailed calculation of size and pressure drop are shown next and in FIGS. 9C and D.

Tube Calculation Continued

Volume of Outer Tube:

$$V_2 = \pi r_{21}^2 l$$

$$V_1 = \pi r_1^2 l$$

Volume of Inner Tube:

$V = $ Volume of silica gel or ascorbic acid Dust $= V_2 - V_1 = \pi r_2^2 l - \pi r_1^2 l$ $$r_2 = \sqrt{\frac{\text{Volume}}{\pi l} + \frac{\pi r_1^2 l}{\pi l}} = \sqrt{\frac{\text{Volume}}{\pi l} + r_1^2}$$

For Volume=2.76 cubic inches (5.5 inches–0.8 inches cylinder)

$r_1 = 0.5$ inch
$l = 3.0$ inches $$r_2 = \sqrt{\frac{2.76}{\pi \times 3} + (0.5)^2} = \sqrt{0.29 + 0.25} = \sqrt{0.54} = 0.73$$

gap=0.23 inches=0.58 cm

Area=$2\pi r l = 2\pi(0.5)(3) = 94$ sq-inches

Equivalent area to disc $3.5^4$ perimeter
Pressure drop=0.5 cm $H_2O$
These equations were then used to evaluate a variety of shaped tubular filters and compared to the disc filter. For example, a 4 inch long tubular filter with an internal radius of 0.5 inch (1 inch id) and an outer annulus diameter of diameter of 1.25 inches would have an outer shell diameter of about 1.75 inches. A tubular filter with this aspect ration would have a pressure drop at 5 l/min of only 0.19 cm $H_2O$, which is equivalent to a 4.5 inch diameter disc. The gap between the tubes, called the annulus, would have a spacing of 0.4 cm. See Table 3 From Table 3, assume that the performance of a disc that is 5 inches in diameter is wanted, which would have an effective surface area of 19.63 sq inches and a pressure drop of 0.12 cm of water. In a tubular version, the same surface area and pressure drop can be achieved with a inside diameter of 0.57 inches and an od of 0.70 inches, provided that the tube was 5.50 inches in length.

Gas Monitoring

Figure 8:
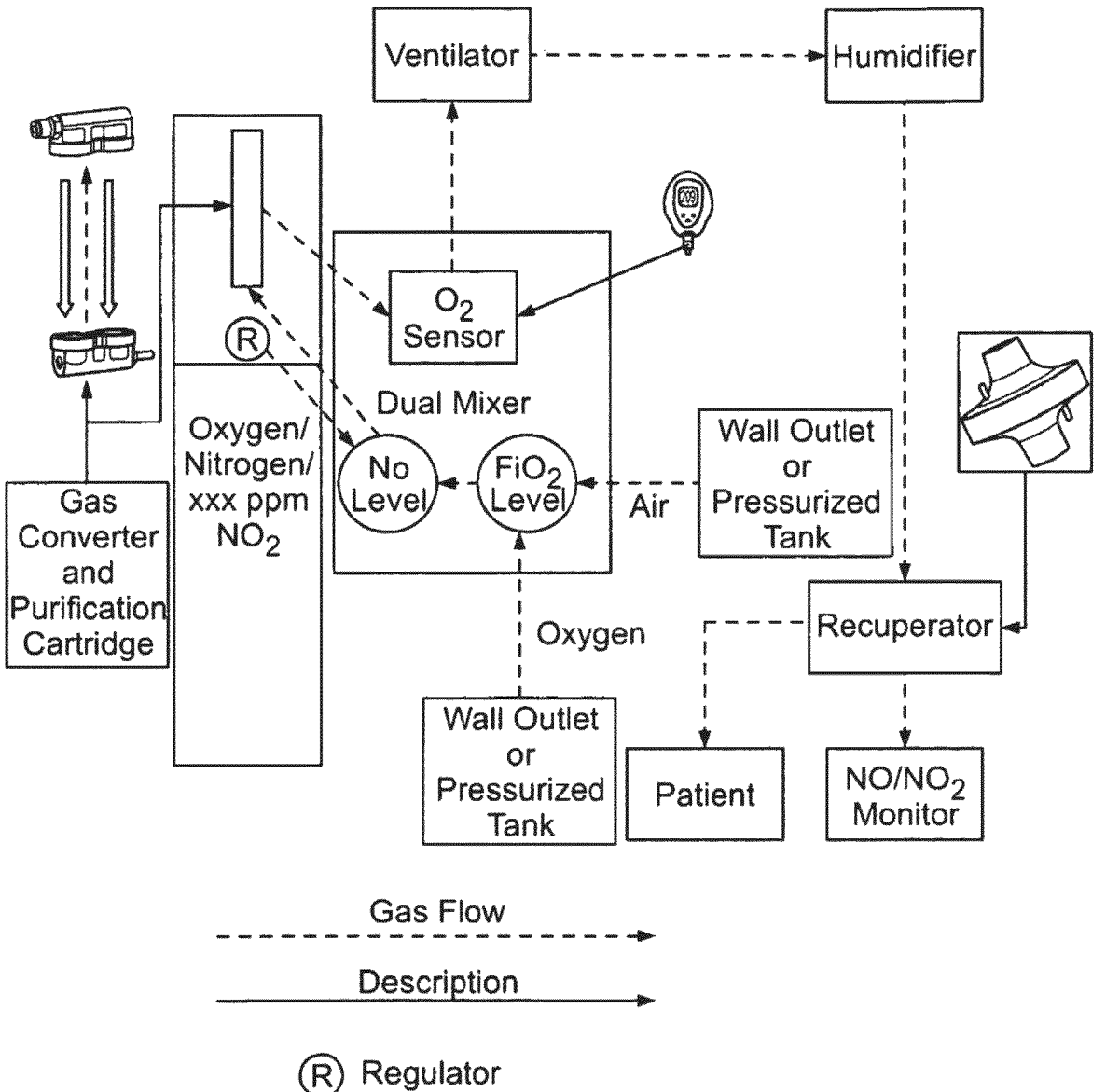
FIG. 8 is a flow diagram depicting nitric oxide delivery for an intensive care unit.

The system may require gas sensors to monitor and display the concentration of NO and $NO_2$ that is delivered to the patient. These can be commercially available monitors and should be equipped with alarm capability. A figurative representation of the system is shown on FIG. 8.

For 100 ppm of NO and 100% oxygen, it is shown by both experiment and calculation that 1.70 ppm of $NO_2$ is formed by the time the sample passes through about 2 meters of tubing, thru a large volume water drop out filter and into the PrinterNox, which is a commercial electrochemical gas analyzer for measuring NO and $NO_2$ for inhalation applications. The sample can also be >100 saturated with water and the water drop out filter is essential. This is a typical problem that is encountered in stack monitoring from incinerator and power plant smoke stacks. There are several possible solutions:

First, heat the sample lines to keep the water in the vapor phase. If the instrument also runs hot, then the water filter can be eliminated and the sampling time reduced, thereby reducing the $NO_2$ formation. It is not a good approach for $NO_2$ sampling since the rate of formation is linear with time and square power with $NO_2$.

Second, sample at the source. This does work, but the condensing water issue remains.

Third, dilute the sample. This does three critical things:

1. It dilutes the sample which reduces the formation of $NO_2$ from NO and $O_2$. This makes sampling down lines possible otherwise most of the NO that is measured at the analyzer will be formed in the sampling lines.

2. It decreases the humidity, which prevents condensation of water in the lines and thereby eliminates the need for a water drop out filter.

3. It reduces the NO level by 50% which brings the machine into the working range of the PrinterNOx detection cells Consider a sample tube with dilution of one (50%).

Initial conditions: 100 ppm NO, 100% oxygen and condensing water (>100%)

With 50% dilution: 50 ppm NO, 60.5% oxygen, and greatly reduced humidity.

At detector: Rate of formation of $NO_2$ reduced by 4*100/60.5=6.6 $NO_2$ reduced from 1.70 to 0.26 ppm With removal of the large volume water condensation filter volume, the level will come down even further.

NO readings are reduced at all concentrations by 50%. This means 20 ppm reads as 10, and 2 ppm reads as 1 ppm. This is corrected for by calibration, but the precision will be reduced by 50%.

$NO_2$ formation in the lines is effectively reduced to zero at normal concentrations. For example, even at 80 ppm NO, the $NO_2$ formed in the lines would be 1.09 ppm without dilution and <0.16 ppm with dilution.

Consider a sample tube with dilution of two (33%).

Initial conditions: 100 ppm NO, 100% oxygen and condensing water (>100%)

With 33% dilution: 33 ppm NO, 47% oxygen, and greatly reduced humidity.

At detector: Rate of formation of $NO_2$ reduced by 9*100/47=20 $NO_2$ reduced from 1.70 to 0.09 ppm NO readings are reduced at all concentrations by ⅓rd. This means 20 ppm reads as 6.67, and 2 ppm reads as 0.67 ppm. This is corrected for by calibration, but the precision will be reduced by ⅓$^{rd}$.

$NO_2$ formation in the lines is effectively reduced to zero at normal concentrations. For example, even at 80 ppm NO, the $NO_2$ formed in the lines would be 1.09 ppm without dilution and <0.05 ppm with dilution.

Humidity

At 37° C., body temperature, the amount of water at 100% relative humidity is 44 g/$M^3$. The air in a hospital is typically at 50% relative humidity and a temperature of 22° C. Air at this temperature contains 10 g/$M^3$.

Diluting one part sample and one part with air from the hospital room would reduce the water concentration in the tube down to 27 g/$M^3$. This amount of water vapor would begin to condense out of the air at a temperature of 28° C. (82° F.).

Diluting one part sample and two parts with air from the hospital room would reduce the water concentration in the tube down to 21.3 g/$M^3$. This amount of water vapor would begin to condense out of the air at a temperature of 23.5° C. (74° F.).

An alternative approach would be to use bone dry air from the wall. This will be available in the same box and could be piped to the sample location by means of a parallel tube.

The detectors are required to run at constant temperature so as to ensure stability. Thus the inside of the detection module would be warm. A 50:50 dilution would work as long as the sample lines were insulated by a thick wall or by having one tube run inside another.

Application (for 50% or 66% Dilution)

The sample tube could be spliced in two (or three), adjacent to the sampling point on the recuperator. Alternatively, the second sampling orifice could be molded into a special adaptor. It would be best not to have a flapping air sample port, since it would raise too many questions from users. This would allow for taking half the sample from the patient inspiratory line and half the sample from the room. Calibration would also have to be at this point. Technically, this would be a perfectly valid way to operate and would meet all regulatory approval guidelines. Naturally, the approach be described in regulatory submissions which would also reference the EPA standard procedures.

Dilution at the sample point is a perfectly viable approach. There would also probably be no need to have the large dead volume water condensation trap on the detector. This would reduce the $NO_2$ formation level even further, by as much as a factor of 5. The life of detector cells would increase from days to about 12 months, even during in house testing. Dilution is the preferred method of sampling the reactive gas stream.

Other Applications

The gas bottle alone can be used for all applications of NO. It is available to deliver the gas without any electronics whatsoever. The advantages of the system are simplicity, no mixing, no electronics and no software. Just connect the regulator and open the valve.

The gas bottle system can also be used with a dilutor. In this case the gas would be shipped as say 1000 ppm of $NO_2$ in oxygen. In a first stage, the user's equipment would then dilute this concentration down to say 20 ppm $NO_2$. The second stage would be to insert the cartridge and convert to NO. this format would be similar to what is currently marketed, but would not require the user to worry about any $NO_2$ that was formed in the gas lines since it would be removed by the recuperator. Similarly, the recuperator cartridge could be used with existing system to convert all of the residual $NO_2$ gas being inhaled into the therapeutic form, namely NO. The recuperator also ensures that no NO gas is lost from the system and that the patient is receiving the full prescribed dose.

The fact that the system can deliver high doses of NO, of the order of 100 to 200 ppm or even higher, without the presence of the toxic form, $NO_2$, may be important. Much of the earlier work was done at doses in the 20 ppm range, but the researchers were always plagued by the presence of toxic $NO_2$. This limited the does that they could go to. With the system all of the $NO_2$ toxicity problems in the inhaled gas are eliminated. This fact alone will greatly increase the utility of NO gas for treatment of a multitude of diseases, and especially ARDS (Acute respiratory distress syndrome).

Other implementations are within the scope of the following claims.

TABLE 1

| | Name | Height Inches | Diameter Inches | Internal Volume L | Weight Pounds | Pressure | Volume L | Max Conc PPM |
|---|---|---|---|---|---|---|---|---|
| LAB | AS | 48 | 8 | 29.45 | 48 | 2000 | 3600 | 100 (124) |
| INCURRENT USE | AQ/BL/88 | 33 | 7.25 | 15.57 | 30 | 2000 | 1918 | 200 (233) |
| LUXFER | ME36 | 25.3 | 4.4 | 4.5 | 8.3 | 3000 | 992 | 400 (450) |

TABLE 2

| | | DISC RECUPERATOR | | | | | | | |
|---|---|---|---|---|---|---|---|---|---|
| | DIAM D INCHES | RADIUS r INCHES | $r^2$ | AREA | $r^4$ | PRESS DROP cm $H_2O$ | mm H2O | THICKNESS INCHES | CM |
| Base case | 0.80 | 0.40 | 0.160 | 0.503 | 0.0256 | 187.00 | 1870.00 | 5.5 | 13.97 |
| | 1.00 | 0.50 | 0.250 | 0.785 | 0.0625 | 76.60 | 765.95 | 3.52 | 8.94 |
| | 1.50 | 0.75 | 0.563 | 1.767 | 0.3164 | 15.13 | 151.30 | 1.56 | 3.97 |
| | 2.00 | 1.00 | 1.000 | 3.141 | 1.0000 | 4.79 | 47.87 | 0.88 | 2.24 |
| | 2.50 | 1.25 | 1.563 | 4.908 | 2.4414 | 1.96 | 19.61 | 0.56 | 1.43 |

TABLE 2-continued

| | | | DISC RECUPERATOR | | | | | |
|---|---|---|---|---|---|---|---|---|
| DIAM D INCHES | RADIUS r INCHES | $r^2$ | AREA | $r^4$ | PRESS DROP cm $H_2O$ | mm H2O | THICK-NESS INCHES | CM |
| 3.00 | 1.50 | 2.250 | 7.068 | 5.0625 | 0.95 | 9.46 | 0.39 | 0.99 |
| 3.50 | 1.75 | 3.063 | 9.621 | 9.3789 | 0.51 | 5.10 | 0.29 | 0.73 |
| 4.00 | 2.00 | 4.000 | 12.566 | 16.0000 | 0.30 | 2.99 | 0.22 | 0.56 |
| 4.50 | 2.25 | 5.063 | 15.903 | 25.6289 | 0.19 | 1.87 | 0.17 | 0.44 |
| 5.00 | 2.50 | 6.250 | 19.634 | 39.0625 | 0.12 const volume | 1.23 | 0.14 | 0.36 |

TABLE 3

| DISC diam INCH | DISC AREA sq inch | DISC PRESS DROP cm-H20 | CYL AREA sq in | CYL IN-SIDE rad inch | CYL OUT-SIDE rad inch | CYL LENGTH inch | CYL GAP cm | CYL PRESS DROP cm H2O |
|---|---|---|---|---|---|---|---|---|
| 2.00 | 3.14 | 4.79 | | | | | | |
| 2.50 | 4.91 | 1.96 | | | | | | |
| 3.00 | 7.07 | 0.95 | 7.23 | 0.50 | 0.79 | 2.30 | 0.75 | 0.95 |
| 3.50 | 9.62 | 0.51 | 9.42 | 0.50 | 0.74 | 3.00 | 0.60 | 0.51 |
| 4.00 | 12.57 | 0.30 | 12.57 | 0.50 | 0.69 | 4.00 | 0.47 | 0.30 |
| 4.50 | 15.90 | 0.19 | 15.58 | 0.62 | 0.78 | 4.00 | 0.40 | 0.19 |
| 5.00 | 19.63 | 0.12 | 19.70 | 0.57 | 0.70 | 5.50 | 0.32 | 0.12 |

What is claimed is:

1. A system for delivering nitric oxide to a patient, comprising:

an apparatus;

a gas source comprising nitrogen dioxide that is delivered to the apparatus, wherein the apparatus converts the nitrogen dioxide to a gas comprising nitric oxide that is delivered to the patient; and at least one safety device comprising a filter, wherein the filter is a particle and/or bacteria filter having a disk or tubular shape, wherein the filter is positioned in a flow path between the apparatus and the patient, and wherein the at least one safety device is further configured to reduce an amount of the nitrogen dioxide in the gas comprising nitric oxide before it is delivered to the patient in an amount below 0.1 ppm.

2. The system of claim 1, wherein the at least one safety device comprises a scavenger material.

3. The system of claim 2, wherein the scavenger comprises proline or diphenylamine.

4. The system of claim 1, wherein the at least one safety device is a recuperator that is operated at atmospheric pressure.

5. The system of claim 4, wherein the recuperator comprises a scavenger.

6. The system of claim 4, wherein the recuperator exhibits a pressure drop of less than 3 cm of water when a gas flow from the gas source is at 60 liter per minute.

7. The system of claim 4, wherein the recuperator has an oxygen concentration in a range of 21% to 100%.

8. The system of claim 4, wherein the recuperator is positioned immediately adjacent to the patient.

9. The system of claim 4, further comprising a sample probe positioned at an exist portion of the recuperator and fluidically connected to a gas analyzer.

10. The system of claim 2, wherein the filter prevents dust from the scavenger material from being delivered to the patient.

11. The system of claim 1, wherein the apparatus further comprises a surface active material.

12. The system of claim 11, wherein the surface active material is a silica gel.

13. The system of claim 12, wherein the filter prevents dust from the silica gel from being delivered to the patient.

* * * * *